US010223786B2

(12) United States Patent
Dickrell, III et al.

(10) Patent No.: US 10,223,786 B2
(45) Date of Patent: Mar. 5, 2019

(54) SYSTEM AND METHOD FOR DIAGNOSING DEFECTS IN RANDOM FLOW SYSTEMS

(71) Applicants: UNIVERSITY OF FLORIDA RESEARCH FOUNDATION, INC., Gainesville, FL (US); SENTINEL DIAGNOSTIC IMAGING, INC., Gainesville, FL (US)

(72) Inventors: Daniel John Dickrell, III, Gainesville, FL (US); Richard D. Clark, III, Gainesville, FL (US); David L. Meadows, Colleyville, TX (US)

(73) Assignees: University of Florida Research Foundation, Inc., Gainesville, FL (US); Sentinel Diagnostic Imaging, Inc., Gainesville, FL (US)

( * ) Notice: Subject to any disclaimer, the term of this patent is extended or adjusted under 35 U.S.C. 154(b) by 136 days.

(21) Appl. No.: 15/302,611

(22) PCT Filed: Apr. 10, 2015

(86) PCT No.: PCT/US2015/025318
§ 371 (c)(1),
(2) Date: Oct. 7, 2016

(87) PCT Pub. No.: WO2015/157641
PCT Pub. Date: Oct. 15, 2015

(65) Prior Publication Data
US 2017/0024886 A1     Jan. 26, 2017

Related U.S. Application Data

(60) Provisional application No. 61/978,493, filed on Apr. 11, 2014.

(51) Int. Cl.
*G06K 9/00* (2006.01)
*G06T 7/00* (2017.01)
(Continued)

(52) U.S. Cl.
CPC ........... *G06T 7/0012* (2013.01); *G01N 21/00* (2013.01); *G06T 7/11* (2017.01); *G06T 7/162* (2017.01);
(Continued)

(58) Field of Classification Search
None
See application file for complete search history.

(56) References Cited

U.S. PATENT DOCUMENTS 8,212,814 B2  7/2012  Branets et al.
8,358,819 B2  1/2013  Wu et al.
(Continued)

OTHER PUBLICATIONS

Budai et al.; "A Public Database for the Evaluation of Fundus Image Segmentation Algorithms"; Gold Standard Database for Evaluation of Fundus Image Segmentation Algorithms, University of Erlangen-Nuremberg in Bavaria, Germany; 2009, Mon. Feb. 25, 2013, 1 page.
Frost et al.; "Retinal vascular biomarkers for early detection and monitoring of Alzheimer's disease"; Transl Psychiatry; 3, e233; 2013, 8 pages.
(Continued)

*Primary Examiner* — Stephen P Coleman
(74) *Attorney, Agent, or Firm* — Thomas | Horstemeyer, LLP

(57) ABSTRACT

Disclosed herein is a method comprising imaging a network section through which flow occurs; where the flow is selected from a group consisting of fluid, electrons, protons, neutrons and holes; partitioning the image into sub-regions based on metabolic need and function; where each region comprises one or more sources and one or more sinks; where the flow emanates from the source and exits into the sinks; performing a Delaunay triangulation tessellation on one or more sub-regions by connecting one or more sources and one or more sinks; where the Delaunay triangulations maximize the minimum angle of all the angles of the triangles in the triangulation; generating a Voronoi diagram from the Delaunay triangulation by subdividing the sub-regions into Voronoi cells, where each Voronoi cell contains exactly one
(Continued)

sink or one source; and where the intersections of Voronoi cells are Voronoi cell vertices; locating a sink endpoint centroid; connecting a source to a nearest Voronoi cell vertex; connecting at least one sink to at least one of the remaining Voronoi cell vortices to complete the network; and performing a smoothing function on the network to form a smoothed network.

17 Claims, 6 Drawing Sheets

(51) Int. Cl.
    *G01N 21/00*     (2006.01)
    *G06T 7/11*     (2017.01)
    *G06T 7/162*     (2017.01)

(52) U.S. Cl.
    CPC ............... *G06T 2207/30101* (2013.01); *G06T 2207/30104* (2013.01); *G06T 2207/30148* (2013.01)

(56) References Cited

U.S. PATENT DOCUMENTS

| | | |
|---|---|---|
| 8,488,863 B2 | 7/2013 | Boucheron |
| 2012/0150048 A1 | 6/2012 | Kang et al. |
| 2013/0138406 A1 | 5/2013 | Khvoenkova et al. |

OTHER PUBLICATIONS

International Search Report for International Application No. PCT/US2015/025318; International Filing Date Apr. 10, 2015; dated Jul. 13, 2015.

Li et al.; "A Piecewise Gaussian Model for Profiling and Differentiating Retinal Vessels"; Image Processing 2003, ICIP 2003, Proceedings. 2003 International Conference on. vol. 1. IEEE; 2003, 4 pages.

Miu, "Lecture 7: Voronoi Diagrams"; Massachusetts Institute of Technology, Computational Geometry Lecture; 2001, Retrieved Jun. 12, 2015, <http://nms.lcs.mit.edu/~aklmiu/6.838/L7.pdf>, 89 pages.

Murray; "The Physiological Principle of Minimumi Work. I. The Vascular System and the Cost of Blood Volume"; Proceedings of the National Academy of Sciences of the United States of America; 12.3, 207; 1926, 8 pages.

Nelson et al.; "High-resolution wide-field imaging of perfused capillaries without the use of contrast agent"; Clinical Ophthalmology; 5; 2011, pp. 1095-1106.

Neuhaus et al.; "Blood viscosity in tube flow: dependence on diameter and hematocrit"; American Journal of Physiology-Heart and Circulatory Physiology, 263(6): H1770(H1778; 1992, 9 pages.

Semba et al.; "The Human Eye Proteome Project: Perspectives on an emerging proteome"; Proteomics; 13; 2013, pp. 2500-2511.

Takahashi et al.; "A mathematical model for the distribution of hemodynamic parameters in the human retinal microvascular network"; J Biorheol; 23; 2009, pp. 77-86.

Written Opinion for International Application No. PCT/US2015/025318; International Filing Date Apr. 10, 2015; dated Jul. 13, 2015, 6 pages.

SYSTEM AND METHOD FOR DIAGNOSING DEFECTS IN RANDOM FLOW SYSTEMS

CROSS REFERENCE TO RELATED APPLICATIONS

This application is a National Stage application of PCT/US2015/025318, filed Apr. 10, 2015, which claims the benefit of U.S. Provisional Application No. 61/978,493, filed Apr. 11, 2014, both of which are incorporated by reference in their entirety herein.

BACKGROUND

This disclosure relates to systems and to methods for analyzing objects that contain a flow field and whose features appear to develop randomly. It relates to systems and to methods for measuring apparent random patterns and pathways in structures that contain flow fields. In particular, this disclosure relates to systems and to methods for imaging and analyzing apparent random patterns and pathways that are contained in a biological system, where the pattern and pathway contains a flow field.

Seemingly or apparent random patterns and pathways are often a part of systems and objects that occur naturally and that generally contain a flow field. An example of a naturally occurring random pathway is a river that travels across the landscape. The river possesses several bends and tributaries and it is often difficult to predict which section of the river will contain a bend or a tributary. Another example of a naturally occurring random pathway is the path taken by blood vessels in the eyeball, the heart, the lungs, the brains, or other parts of a living being. Blood vessels have a number of branches and it is difficult to predict where these branches will occur, the number of branches and the average orientation of these branches that a particular part (e.g., the heart, the eyeball, and the like) of a particular living being will have. A tree is another example of a naturally occurring structure whose branches take random pathways and the point of contact of one branch with another is an apparently random event. All of the aforementioned examples—the river, the blood vessels and the tree contain flow fields.

The ability to determine and to measure the structure of such apparently random objects permits predictive capabilities for the design of future objects. It also permits a comparison of one set of the objects (that are grown or developed under one set of circumstances) with another set of equivalent objects (that are grown or developed under a second set of circumstances). It is therefore desirable to develop methods that can be used to measure the structures and to quantify their features so that they can be compared with one another and to predict the behavior of future objects.

SUMMARY

Disclosed herein is a method comprising imaging a network section through which flow occurs; where the flow is selected from a group consisting of fluid, electrons, protons, neutrons and holes; partitioning the image into sub-regions based on metabolic need and function; where each region comprises one or more sources and one or more sinks; where the flow emanates from the source and exits into the sinks; performing a Delaunay triangulation tessellation on one or more sub-regions by connecting one or more sources and one or more sinks; where the Delaunay triangulations maximize the minimum angle of all the angles of the triangles in the triangulation; generating a Voronoi diagram from the Delaunay triangulation by subdividing the sub-regions into Voronoi cells, where each Voronoi cell contains exactly one sink or one source; and where the intersections of Voronoi cells are Voronoi cell vertices; locating a sink endpoint centroid; connecting a source to a nearest Voronoi cell vertex; connecting at least one sink to at least one of the remaining Voronoi cell vortices to complete the network; and performing a smoothing function on the network to form a smoothed network.

Disclosed herein is a system for performing a constructal analysis, the system comprising a processor and a memory to perform a method comprising initiating capture of an image of an apparent random pathway, pattern, or network in a subject; where the apparent random pathway, pattern or network comprises a flow field; partitioning the image into sub-regions based on metabolic need and function; where each region comprises one or more sources and one or more sinks; where the flow emanates from the source and exits into the sinks; performing a Delaunay triangulation tessellation on one or more sub-regions by connecting one or more sources and one or more sinks; where the Delaunay triangulations maximize the minimum angle of all the angles of the triangles in the triangulation; generating a Voronoi diagram from the Delaunay triangulation by subdividing the sub-regions into Voronoi cells, where each Voronoi cell contains exactly one sink or one source; and where the intersections of Voronoi cells are Voronoi cell vertices; locating a sink endpoint centroid; connecting a source to a nearest Voronoi cell vertex; connecting at least one sink to at least one of the remaining Voronoi cell vortices to complete the network; and performing a smoothing function on the network to form a smoothed network.

DETAILED DESCRIPTION

Figure 1:
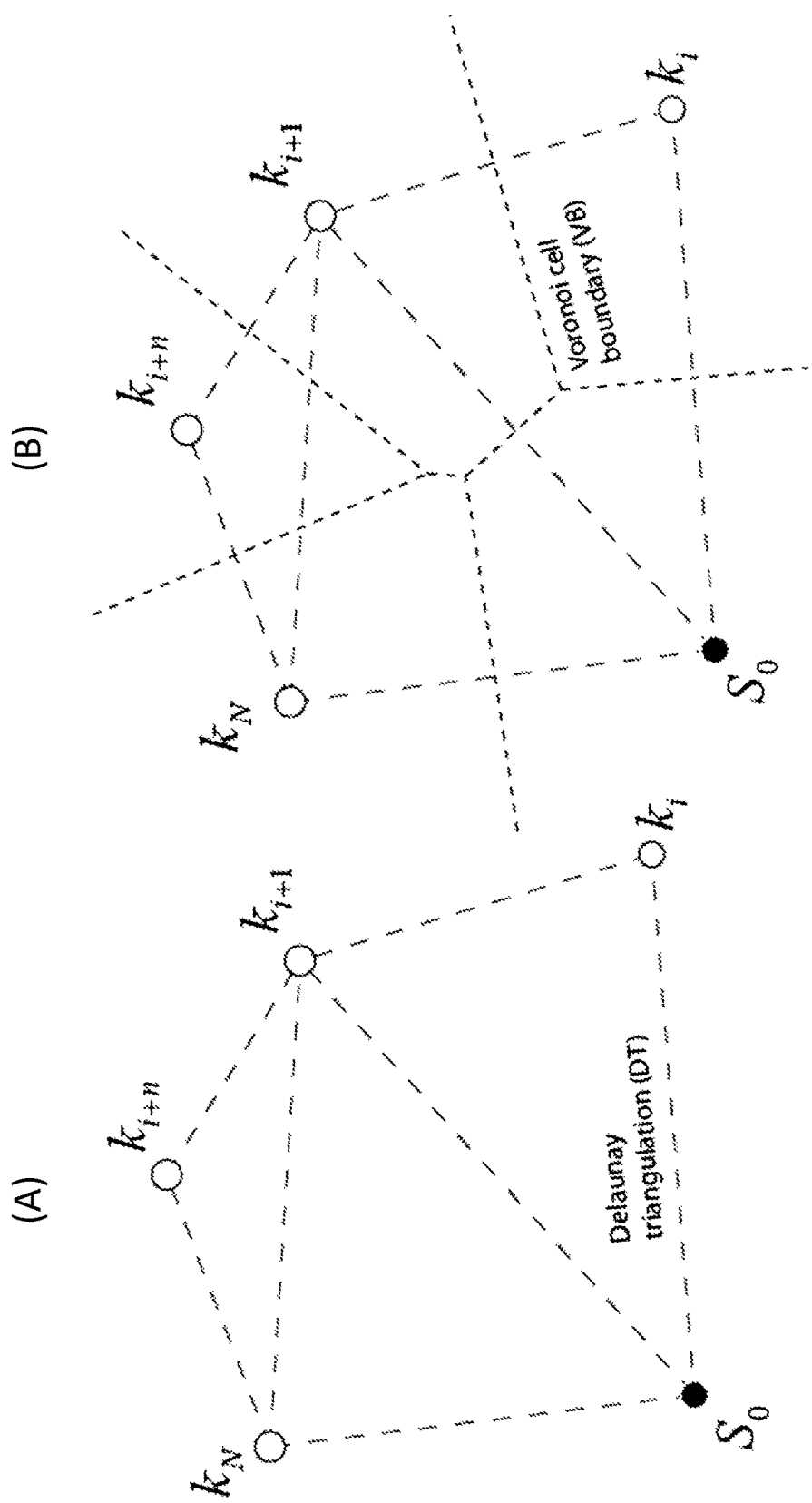
FIG. 1A is a depiction of a Delaunay triangulation (DT) tessellation connecting the source and sink delivery locations.
FIG. 1B is a Voronoi diagram (VD) that is generated from the Delaunay triangulation.

Disclosed herein is a system that can be used to analyze images of objects that contain an apparently random pattern or network that contains a flow field. This system imports an image (e.g., a medical image, a topographical image of a stream or a river, electrical circuitry where electrical percolation is desirable, or the like) and uses spatial analysis methods (e.g., Voronoi diagrams, Delaunay triangulations, network topology, and the like) to determine the organization of biological or other topographical structures contained in the image and combines the spatial analysis with quantitative performance metrics of the imaged structure to determine its performance. This analysis of the performance of the flow field can then be used to determine whether the flow field is performing efficiently (i.e., it is upto par) or performing inefficiently (i.e., it is diseased or damaged). In another embodiment, the analysis can provide information on how to enable an improved performance of the flow field.

In another embodiment, the system and the method disclosed herein employs biomarkers in order to facilitate an understanding of the performance of a given biological system. A biomarker, or biological marker, as used herein refers to a measurable indicator of some biological state or condition. Biomarkers are measured and evaluated to examine normal biological processes, pathogenic processes, or pharmacologic responses to a disease, to damage occurring in tissues or as the result of therapeutic intervention.

The method is advantageous in that it can be applied to any apparently random pattern, pathway, or network whose connections can be calculated and performance can be measured. Apparent random patterns, pathways, or networks are capable of being analyzed by this method to diagnose improper functions and disease. A novel aspect of this disclosure is the combination of spatial feature imaging with functional performance metrics (e.g., the flow resistance or conductance, flow volume, pressure and viscosity of fluid, and the like) in a computational tool that can directly diagnose medical abnormalities from the raw input image. The method can also be used to design and to synthesize prosthetics (or replacement parts) for existing organisms or to correct for damages in other flow systems (e.g., streams, rivers, complex electrical circuits, semiconductors, and the like).

In an exemplary embodiment, the method can be used to estimate brain function and brain morphology and topology. It can also be used to distinguish functional portions of the brain from damaged or non-functional portions of the brain. For example, a functional magnetic resonance image (fMRI) of a human brain shows local regions of activity within the three-dimensional volume of the brain Using the spatial distribution of the areas of interest within the brain extracted from the image (the interconnected-ness of the regions) and combined with the performance metrics (from the fMRI analysis) this method would quantitatively determine differences between healthy brain activity and unhealthy brain activity. While the foregoing is directed to describing how the brain may be analyzed, the system and the method are not restricted to examining the brain, but can be used to analyze other parts of the body such as the eyes, the lungs, the heart and other parts of the vascular system. This method of analysis may also be used to repair other flow systems (e.g., streams and rivers that have been damaged from floods, droughts, and the like).

In another embodiment, the system and the methods described herein can be used to measure the apparently random pattern, pathway, or network and be used to characterize its features such as its end to end distance, its radius of gyration, its tortuosity, the ability of the structure to permit a fluid to flow through it, atomic and sub-atomic particles (e.g., electrons, protons, photons, holes, and the like), energy, and the like, to flow through it. In one exemplary embodiment, features of the random pattern, pathway, or network can be characterized using spatial analysis so long as it involves a flow along the apparently random pattern, pathway, or network. The system disclosed herein can also be used to deduce information about the neighborhood surrounding the apparently random patterns, pathways, and networks. It can also be used to study the events surrounding a series of events so long as the series of events are affected by the event.

The term "seemingly" or "apparent" or "apparently" is used because the pathways, patterns or networks described herein appear to be random (i.e., they have tortuous pathways that appear to be random), but can actually be characterized using thermodynamic concepts such as the "efficiency of the system" "boundary conditions", "energy minimization", "guiding forces", "design constraints", "minimization of losses" or the like. The apparent pathway, pattern or network may also be characterized as a naturally occurring pathway, pattern or network and comprises a flow field. It can also be called a transport network since it transports a fluid, atomic and sub-atomic particles, energy, or the like.

The term "seemingly" or "apparent" or "apparently" is used because the pathways, patterns or networks described herein can be mathematically characterized in addition to being statistically characterized. A truly random pattern or network can only be statistically characterized, while a seeming or apparent network can be mathematically characterized without the use of statistical terms such as standard deviations, mean, and the like. The mathematical characterization involves transport parameters of the system such as flow conductance or resistance, flow volume, flow viscosity, sedimentation rate, or the like in addition to structural parameters such as the radius of gyration, tortuosity, number of contact points between different sections of the network, and the like.

The resulting analysis and the data obtained therefrom can be used to compare a first random pattern, pathway, network, or a series of events with a second random pattern, pathway, network, or a series of events that is grown or developed under different circumstances, or at another location, or at another time in the same or different location. The comparison can be used to assess the quality of the first random pattern, pathway, network, or a series of events with respect to the second random pattern, pathway, network, or series of events. The resulting analysis, the data obtained therefrom and any data pertaining to the comparison can be transmitted to a screen, printed out on a sheet, saved and stored on a solid state drive, a hard disc drive or a floppy disc. In an embodiment, the resulting analysis, the data obtained therefrom and any data pertaining to the comparison may be used in prescribing a course of treatment or therapy that involves the administering of dosages of medicine, deploying stents to improve the flow of vascular fluids, performing surgery, performing surgery that includes bypass surgery, construction of models to mimic the degradation of the vascular system, construction and replacement of a part of the body with synthetic prosthetics that replicate the existing diseased part, construction and replacement of a part of the body with synthetic prosthetics that are based on the use of constructal principles (which do not necessarily replicate the diseased part), and the like.

The system comprises an imaging device in operative communication with a computer that contains code or software to analyze a portion of the image and to provide various parameters that characterize the pathway, pattern, network, or random series of events. The code or software comprises an image processing algorithm that can measure one or more features of the image and can provide details about an analyzed feature of the image using constructal analysis.

Disclosed herein too is a method that can be used to analyze images of objects that contain a random pattern, pathway, network, or series of events. The method comprises capturing an image of a random pathway, pattern, network, or a series of events, or the like. The image is then transmitted to a computer (e.g., a device having a memory and a processor) where an algorithm may be initiated to generate parameters of the image as detailed below. These parameters can be used to determine the quality or condition of the object.

As noted above, the method comprises obtaining an image of the organ (e.g., heart, eye, brain, lung, and the like) or object (e.g., semiconductor, non-intrinsically conducting electrical materials such as conductive polymers, and the like). The image of the organ or object is partitioned into sub-regions based on metabolic need and function. For example, if the image is one of the brain, its metabolic need is glucose and it's function is to transmit neurons. The needs of the sub-regions are then determined. The needs of the sub-regions are determined on a volumetric basis (e.g., amount of glucose per unit volume or volumetric blood flow), on a functional basis (e.g., neurons per unit of glucose), or the like. It is to be noted that this approach is also applicable to electrical or pneumatic distribution in systems that use electricity and or fluids for functioning.

The subdividing of the image may be conducted by a variety of different methods. For example, given the source $S_o$ and sink $k_{1\ldots N}$ locations of an arterial network, a Delaunay triangulation (DT) tessellation connecting the source and sink delivery locations may be constructed. A Delaunay triangulation for a set P of points in a plane is a triangulation DT(P) such that no point in P is inside the circumcircle of any triangle in DT(P). Delaunay triangulations maximize the minimum angle of all the angles of the triangles in the triangulation. In other words, the Delaunay triangulation of a point set is a collection of edges satisfying an "empty circle" property: for each edge a circle can be found that containing the edge's endpoints but not containing any other points.

A Voronoi diagram (VD) is generated from the Delaunay triangulation, subdividing the larger region into sub-regions. A Voronoi diagram is a geometric structure that represents proximity information about a set of points or objects. Given a set of sites or objects, the plane is partitioned by assigning to each point its nearest site. The points whose nearest site are not unique, form the Voronoi diagram. That is, the points on the Voronoi diagram are equidistant to two or more sites. So for a set S of n sites, the Voronoi diagram VD(S) is the partition of the plane into blocks of points with the same nearest site or sites.

FIG. 1(A) is a depiction of a Delaunay triangulation (DT) tessellation connecting the source and sink delivery locations while FIG. 1(B) is a Voronoi diagram (VD) that is generated from the Delaunay triangulation.

Each sub-region, or Voronoi cell (VC), contains exactly one sink (or source depending if it is an arterial or venous network). The intersection of VC's are labelled as a Voronoi cell vertices (VCV).

Figure 2:
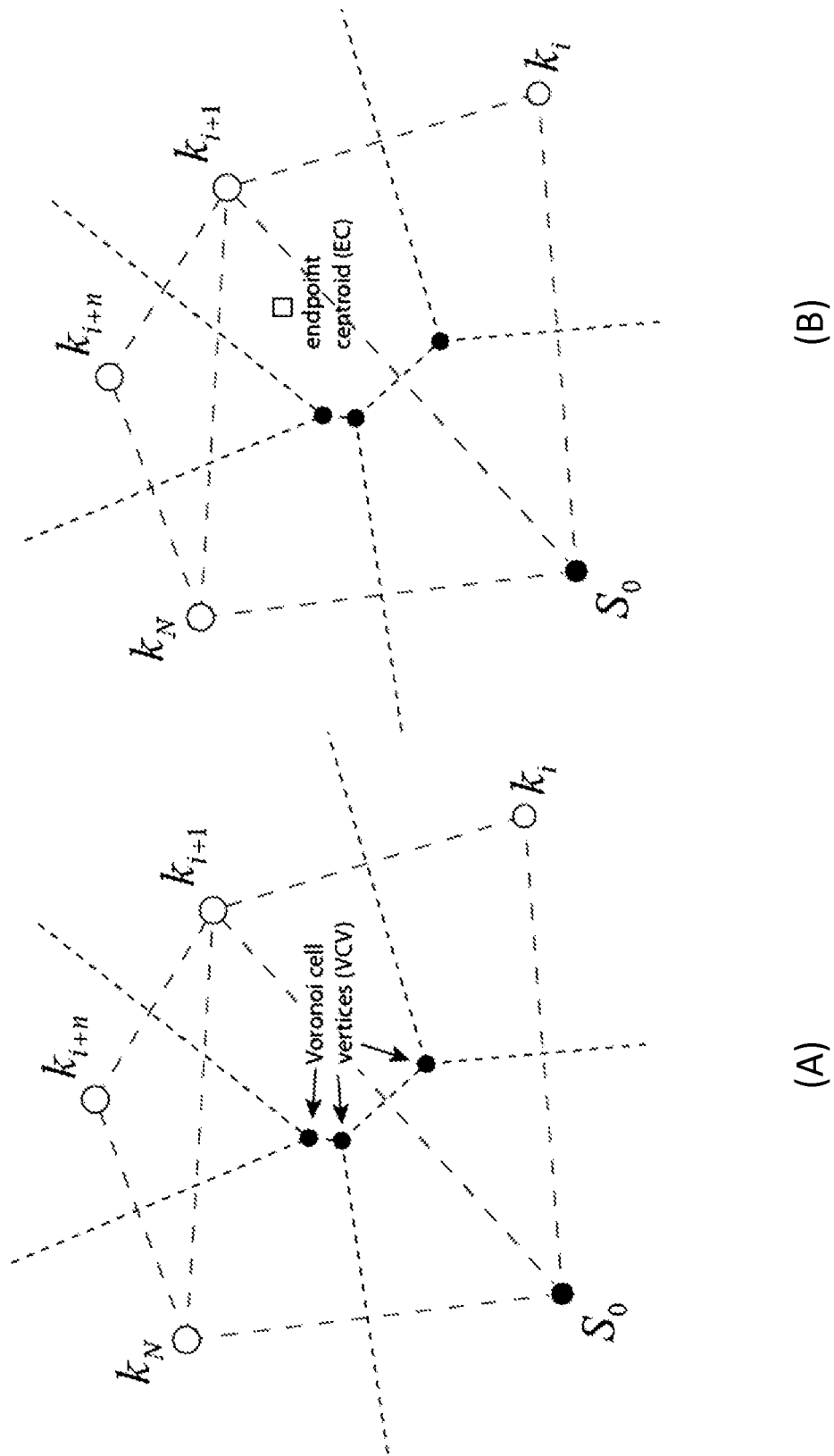
FIG. 2A is a depiction of the Voronoi cell vertices.
FIG. 2B depicts the centroid of the endpoints.

These VCV locations in space are points which are simultaneously equidistant from arterial sink locations. The sink endpoint centroid location is calculated, establishing a bias direction to start the network. FIG. 2(A) is a depiction of the Voronoi cell vertices while the FIG. 2(B) depicts the centroid of the endpoints.

Figure 3:
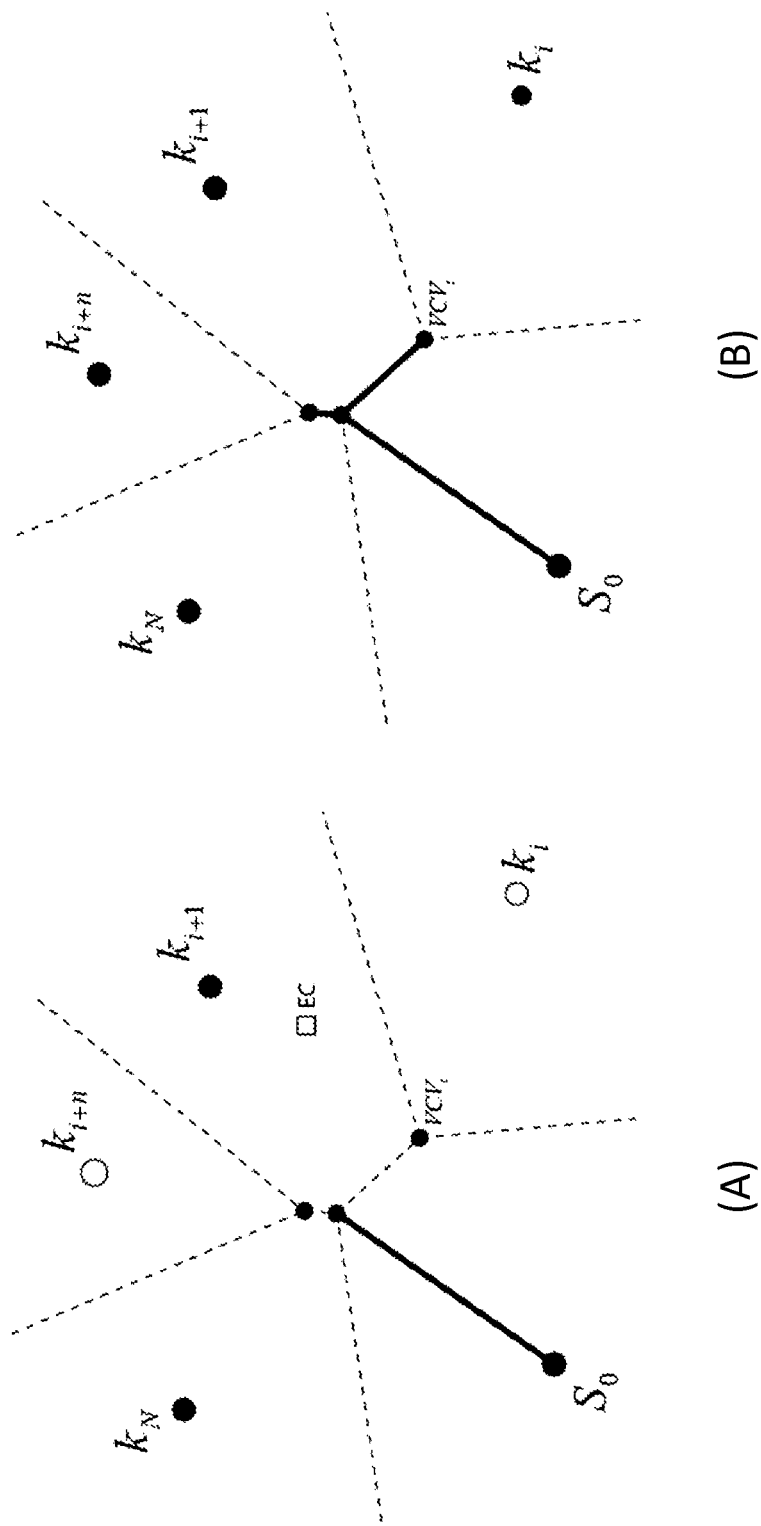
FIG. 3A depicts the connecting of the first vessel to the nearest VCV.
FIG. 3B depicts some of the successive connections to the VCV's until all of the sink endpoints are "closed"

The first vessel connects the source to the nearest VCV. FIG. 3(A) depicts the connecting of the first vessel to the nearest VCV. This begins the network. Each VCV visited closes some of the sinks from the "open" (or unvisited list), denoted by a black circle. Successive connections to VCV's are made until all of the sink endpoints are "closed". FIG. 3(B) depicts some of the successive connections to the VCV's until all of the sink endpoints are "closed".

Figure 4:
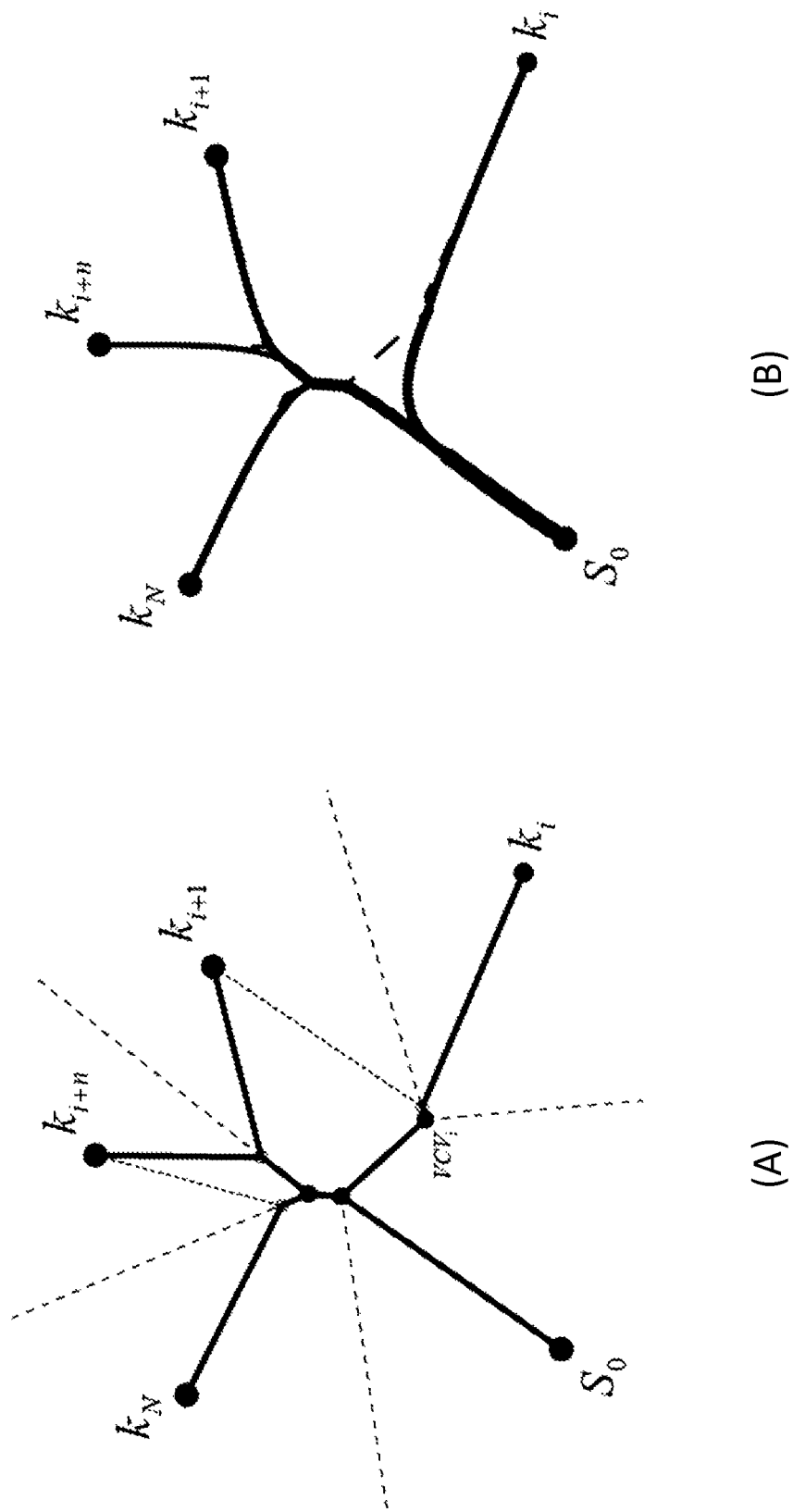
FIG. 4A depicts the formation of the network backbone after all of the sink endpoints are created.
FIG. 4B depicts the resultant path after the smoothing of paths after Bezier curves is completed.

Once all of the sink endpoints are closed, a network backbone has been created. FIG. 4(A) depicts the formation of the network backbone after all of the sink endpoints are created. Each endpoint must now be connected to the backbone by determining the most efficient combination of bifurcations bridging the backbone to each sink endpoint. After the sink endpoints are connected to the backbone, the overall connectivity network is complete. The vascular network is completed by enlarging the individual segment diameters to accommodate the necessary flow to be delivered to each sink endpoint. Vessel curvature is accomplished by smoothing the paths using Bezier curves that minimize the instantaneous changes in velocity along the path from source to sinks while simultaneously minimizing the total vascular material used. FIG. 4(B) depicts the resultant path after the smoothing of paths after Bezier curves is completed.

After the smoothing of the curves, various parameters may be estimated from the mathematically created network. These include end to end distance of the network, radius of gyration of the network, junction angles associated with another part of the random pathway, vessel widths, vessel lengths, vessel tortuosities, junction exponents, asymmetry ratios, area ratios, parent—child angle changes, parent—child vessel diameter ratios—child—child diameter ratios, overall links/volume of observable vasculature, metrics as a function of vessel generations, metrics as a function of location, and the like.

As noted above, the system disclosed herein employs biomarkers. When a biological system is under consideration, the following biomarkers are used in arteries and in veins: segment (sections of the artery or vein under consideration) diameters, segment lengths, segment generations, asymmetry index, segment flow rates, bifurcation angles (where one portion of an artery or vein contacts another portion of the artery or vein), total vessel (artery or vein) volumes, junction (branching) exponents (one example of which are fractal dimensions), segment tortuosities, overall network tortuosity, apparent network conductance, junction locations in relation to OD (outer diameter)/fovea, junction spatial distributions, vessel terminus locations, vessel terminus spatial distributions, vessel dropout, vessel stenosis, or the like. In the case of the aforementioned biomarkers, the arteries or veins form the network which is the analyzed in terms of the biomarkers.

The methodology employed through constructal analysis involves understanding and determining the initial conditions, boundary conditions and operating constraints for optimizing the flow in an apparently random pathway, pattern or network. Vital sign data specific to each individual used for the initial and boundary conditions is also obtained. The image of the individual vasculature is also obtained. The medical image is then translated into a mathematical topological network to calculate the flow-related performance metrics (volumetric flow rates, velocities, vessel stresses, and the like.) at all nodes/segments of the network if the inlet pressure to the network is proportional to an applied pressure. The optimal network morphology that will yield the minimum global resistance to flow for the same individual operating constraints and input conditions is determined. The flow efficiency of a real network (e.g., a vascular network) can then be compared to the theoretical optimal-design network flow.

In one embodiment, the size, flow characteristics, volume, and other aspects of the various vessels in the vascular structure of a living being can be identified and quantified. Accordingly, by employing various fluid dynamics theories as well as spatial analysis theory and constructal analysis, an optimal flow angle associated with various junctions in the vascular network can be calculated. Therefore, an analysis of healthy patients as well as those diagnosed with certain conditions can yield various statistical measures with which an analysis of the vascular system can be correlated to aid in the diagnoses of certain conditions. It should be appreciated that an embodiment of the disclosure can calculate one or more measures associated with path length, tortuosity as well as a constructal analysis of the vascular network of the vascular system and, in combination, correlate one or more of these measures with healthy patients and/or those diagnosed with certain conditions.

For example, the vessel radius of each vessel in a skeletonized retinal network can be determined from an image analysis of the smoothed network. The endpoints of each vessel are designated as a "ground" pressure, and resistances are determined from vessel length and radius, which assumes a steady, laminar flow of an ideal Newtonian fluid. While some fluids are characterized as being Newtonian fluids, the systems and methods disclosed herein are not always necessarily Newtonian fluids. Non-Newtonian fluids may also be used so long as the appropriate analysis is applied. For example, if blood (a non-Newtonian) flows through the vessels, then the appropriate constitutive equations for blood are to be used to obtain accurate information. Accordingly, these measures can be detected in a subject and compared with typical measures in patients with various diagnoses of certain conditions. Correlations can then be made that may aid in the diagnosis of certain conditions.

It should be noted that while the examples discussed herein illustrate a constructal analysis of blood flow through the vascular network of a retina, the same analysis can be undertaken on any biological system within the body as well as with respect to any type of biological materials. For example, such a constructal analysis can be performed on a brain with respect to blood flow through the brain. As an additional example, the techniques discussed herein can also be applied to an analysis of one or more lungs of a patient with respect to blood flow and/or airflow through the one or more lungs. It can also be applied to the flow of electrons through nerves fibers. Other variations and permutations of a system and a material under analysis should be appreciated.

Embodiments of the present disclosure can be implemented as logic executed in one or more computing devices. A computing device according to the disclosure can include at least one processor and a memory, both of which are in electrical communication with a local interface. To this end, the computing device may comprise, for example, at least one server computer or like device. The local interface may comprise, for example, a data bus with an accompanying address/control bus or other bus structure as can be appreciated.

Stored in the memory are both data and several components that are executable by the processor. In particular, stored in the memory and executable by the processor is an application implementing logic according to the present disclosure as well as potentially other applications. It is understood that there may be other applications that are stored in the memory and are executable by the processors as can be appreciated. Where any component discussed herein is implemented in the form of software, any one of a number of programming languages may be employed such as, for example, C, C++, C#, Objective C, Java, Javascript, Perl, PHP, Visual Basic, Python, Ruby, Delphi, Flash, or other programming languages.

A number of software components are stored in the memory and are executable by the processor. In this respect, the term "executable" means a program file that is in a form that can ultimately be run by the processor. Examples of executable programs may be, for example, a compiled program that can be translated into machine code in a format that can be loaded into a random access portion of the memory and run by the processor, source code that may be expressed in proper format such as object code that is capable of being loaded into a random access portion of the memory and executed by the processor, or source code that may be interpreted by another executable program to generate instructions in a random access portion of the memory to be executed by the processor, etc. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory is defined herein as including both volatile and nonvolatile memory and data storage components. Volatile components are those that do not retain data values upon loss of power. Nonvolatile components are those that retain data upon a loss of power. Thus, the memory may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor may represent multiple processors and the memory may represent multiple memories that operate in parallel processing circuits, respectively. In such a case, the local interface may be an appropriate network that facilitates communication between any two of the multiple processors, between any processor and any of the memories, or between any two of the memories, etc. The local interface may comprise additional systems designed to coordinate this communication, including, for example, performing load balancing. The processor may be of electrical or of some other available construction.

Although executable logic of an embodiment of the disclosure may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application according to an embodiment of the disclosure that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

The data can be stored on the cloud and can be made accessible to specialists across the world. This will permit remote access of images and testing of patients in remote regions across the world. Storage of data on the cloud can be used to compare behavior or morphology in normal populations versus diseased populations and to aggregate such statistics in mass populations.

The system and method disclosed herein is used to evaluate automated fundus photographic analysis algorithms of a computer-assisted diagnostic system for grading diabetic retinopathy, to evaluate therapeutic responses of anti-angiogenic drugs in choroidal neovascularization, to evaluate optic neuritis along with degeneration of the retinal nerve fiber layer that is highly associated with multiple sclerosis, to evaluate ocular migraines associated with systemic vascular disease and high blood pressure, to evaluate the condition of blood vessels and/or nerves when affected by hypertension, chronic kidney failure, atherosclerosis, pulmonary diseases such as emphysema, chronic bronchitis, asthma, chronic obstructive pulmonary disease, interstitial lung disease and pulmonary embolism, cardiovascular diseases, myocardial infarction, aneurysms, transient ischemic attack, brain diseases, concussions, Alzheimer's disease and/or strokes.

The constructal analysis method can be detailed as follows. The processing of the image begins by obtaining a binary image of an isolated arterial or venous network. The image is a pixelated image with white pixels being equivalent to the vasculature and dark pixels representing the background. A determination is made of the total number of particles (discrete areas of white pixels) and other pixels (i.e. all particles) but the one comprising of the most pixels are removed. In other words, the imaged vasculature is smoothed out to a series of points that represent the highest pixel density along the path of the vasculature. A thinning algorithm is then used that reduces the network to paths with widths of one pixel. Any "spurs" or small lengths of network containing endpoints are then removed. A flow source (i.e., a series of interconnected arteries or veins through which flow occurs) in the image is then used for further study by manually selecting a suitable area in the image as follows.

Manually select the left and right edges of the optic disc to determine a pixel-to-micron ratio based on a diameter of 1.76 mm. Determine all endpoints and junctions in the network by analyzing each vascular pixel's connectivity to neighboring pixels. Define the network by "walking" along the vascular network from each junction. The following are determined:

Nodes—junctions, endpoints, or the flow source area.
Segments—lengths of pixels connecting nodes The width of all segments in the vascular network in the optical disc are determined by performing a principal component analysis on the thinned segment, then taking N perpendicular measurements along the segment in the binary image and averaging the measurements. N is generally between 3 and 7. Determine the lengths of segments by accumulating and summing up pixel-to-pixel lengths from one end of a segment to the other. To pixels sharing a side of the segment add a length of 1.0 while for pixels sharing a corner of the segment, add a length of 1.41 multiplied by the length of the side of the pixel.

Determine the generation of each segment by attributing a generation number of "1" to each segment connected to the flow source. Each bifurcation thereafter adds a generational number to the child segments. For example, a child segment that branches of a main segment is given the number 1, while a $2^{nd}$ child segment that branches of the $1^{st}$ child segment is given the number 2, and so on. Determine the viscosity in each segment based on its diameter and an assumed hematocrit level. The haematocrit (Ht or HCT), also known as packed cell volume (PCV) or erythrocyte volume fraction (EVF), is the volume percentage (%) of red blood cells in blood. It is normally about 45% for men and 40% for women. It is considered an integral part of a person's complete blood count results, along with hemoglobin concentration, white blood cell count, and platelet count. Determine the fluid conductance in each segment using the Hagen-Poiseuille equation.

In short, as detailed above, after isolating a portion of a binarized vascular system (or an equivalent flow system such as a river, and the like), extraneous rough edges and small segment lengths are removed. Segment widths and lengths are calculated and each generational segment is assigned a numerical value depending upon its location from the main segment. The viscosity of fluids being transported through the segments is then computed. The flow in each segment and in the entire binarized vascular system is then determined using the Hagen-Poiseuille equation.

$$\Delta P = \frac{8\mu L Q}{\pi r^4} \qquad (1)$$

where ΔP is the pressure loss through the segment; L is the length of segment; μ is the dynamic viscosity; Q is the volumetric flow rate through the segment; and r is the radius of the segment.

For each segment endpoint, determine a virtual bifurcating network whose relative diameter is a function of Murray's Law and relative length is a function of data found in the literature. Murray's law, or Murray's principle is a formula for relating the radii of child segments to the radii of the parent segment of a lumen-based system. The branches classically refer to the branching of the circulatory system or the respiratory system, but have been shown to also hold true for the branching of xylem, the water transport system in plants.

Murray's analysis facilitates a determination of the segment radius that minimizes expenditure of energy by the organism. Larger vessels lower the energy expended in pumping fluid (e.g. blood, water, and the like) because the pressure drop in the vessels reduces with increasing diameter according to the Hagen-Poiseuille equation. Larger vessels increase the overall volume of fluid flowing through the system. In the event, that the system is a vascular system (i.e., one that transports blood), increasing the flow of blood means increasing metabolic support. Murray's law helps balance these factors.

For n child segments arising from a common parent segment, the formula is:

$$r_p^3 = r_{c1}^3 + r_{c2}^3 + r_{c3}^3 + \ldots r_{cn}^3$$

where $r_p$ is the radius of the parent segment, and $r_{c1}$, $r_{c2}$, $r_{c3}$, and $r_{cn}$ are the radii of the respective child branches. From Murray's law, it may be seen that larger diameter tubes are heavier because of both the tubing and the additional volume of enclosed fluid, but the pressure losses incurred are reduced and so the mass of the pumping system that is used can be lower. The (inner) tube diameter $d_i$ which minimizes the total mass (tube+fluid+pump), is given by the following equation in laminar flow:

$$d_i^6 = \frac{1024\mu Q^2}{\pi^2 K \rho TUBE(C^2 + C) + \rho FLUID}$$

where Q is the volume flow rate, μ is the fluid viscosity, K is the power-to-weight ratio of the pump, ρTUBE is the density of the tubing material, c is a constant of proportionality linking vessel wall thickness with internal diameter and the ρFLUID is the density of the fluid.

For turbulent flow the equivalent relation is $$d_i^7 = \frac{80 Q^3 f \rho FLUID}{\pi^3 K \rho TUBE(C^2 + C) + \rho FLUID}$$

where f is the Darcy friction factor. The junction relations above can therefore be applied in the following form in turbulent flow:

$$r_p^{7/3} = r_{c1}^{7/3} + r_{c2}^{7/3} + r_{c3}^{7/3} + \ldots + r_{cn}^{7/3}$$

The binary image of the network is bifurcated down to approximately segments having diameters of approximately 5.0 micrometers. A conductance is calculated for each virtual network (binarized image) by using serial/parallel relationships for the different virtual segments. The conductances for parallel segments are added while the reciprocal of conductances for serial segments are added to produce an equivalent conductance. This method is used on the entire vascular network to determine a total equivalent conductance. If a pressure is assigned to the source node and a pressure assigned to the capillary level, a series of linear equations can be used to determine the flow rate and pressure at every segment and junction. If the flow rates and pressures are known through the entire network, the velocity, Reynolds number, shear rates and shear stresses can be calculated using fundamental fluid equations.

Alternatively, once the flow rates and pressure at every segment and junction are known, one can design a new network, where fluids travel through the system with predetermined velocities, shear rates, shear stresses and Reynolds number. The knowledge of rates of fluid flow, shear stresses and shear rates, in a particular vascular system can also be used to determine whether a particular vascular system is diseased without necessarily imaging the system.

In addition, a knowledge of the rates of fluid flow, the Reynolds number, the conductances, the resistance to flow, the shear stresses and shear rates, and the like, in a particular vascular system can also be used to predict defects in vascular systems in the eyes, lungs, heart and the like.

Example 1

The following example is a non-limiting description of the system and the method disclosed herein.

Approximately 50 million fundus photographs are taken annually in the US and is expected to grow at an increasing rate. To address the growing burden on specialists and the increasing need for faster evaluation of these photographs, the method disclosed herein can be used to analyze the geometric, morphological and flow-related properties of the vascular network. This technology identifies new, quantitative imaging biomarkers for ophthalmic and systemic diseases and associated risk factors.

Forty five fundus photographs from the High-Resolution Fundus Image Database at the University of Erlangen-Nuremberg (http://www5.cs.fau.de/research/data/fundus-images/) that are fovea-centered with a field-of-view of 60 degrees were used for this study. The fovea centralis is a small, central pit composed of closely packed cones in the eye. It is located in the center of the macula lutea of the retina.

Each photograph is categorized as healthy, diabetically retinopathic or glaucomatous. For every photograph, there was an accompanying manual segmentation of the vasculature from which the arterial and venous networks were identified and separated. The networks were analyzed to determine vessel geometries as well as vessel connectivity, which is used to calculate the total fluid conductance of the network through a series of linear algebraic operations. The apparent total blood flow was calculated for each network using a constant pressure gradient between the central vessel and capillaries. We compared the geometric, morphological and flow-related properties of arterial and venous networks from 15 healthy patients to those of 15 retinopathic patients and 15 glaucoma patients.

In the three sample populations (healthy, diabetic retinopathy and glaucoma patients) the absolute distributions, relative distributions and cumulative distributions were analyzed for the following biomarkers in the images of the arteries and in the veins:

Segment diameters
Segment lengths
Segment generations

Asymmetry Index
Segment flow rates
Bifurcation angles
Total vessel volumes
Junction exponents
Segment tortuosities
Overall network tortuosity
Apparent network conductance
Junction locations in relation to OD/fovea
Junction spatial distributions
Vessel terminus locations
Vessel terminus spatial distributions
Vessel dropout
Vessel stenosis Additionally, flow density maps were prepared using Voronoi analysis and hypoxia/ischemic thresholds and indices assigned for diabetic retinopathy and glaucoma. The supplementary document provides a partial compilation of these the distribution plots for each biomarker described above.

These individual biomarkers, or combination of multiple biomarkers, greatly enhance the sensitivity and specificity of detecting ophthalmic, systemic, neurological, or cerebral diseases, not limited to:
1. Diabetic retinopathy
2. Macular degeneration (wet and dry)
3. Glaucoma
4. Central vein occlusion
5. Peripheral vein occlusion
6. High blood pressure
7. Retinal hemorrhages
8. Atherosclerosis
9. Retinal neovascularization
10. Multiple sclerosis
11. Alzheimer's disease
12. Coronary disease
13. Carotid artery/vein occlusion Apparent Total Blood Flow Capacity The average apparent total blood flow in healthy arterial networks was 64.9+/−13.7 microliters per minute while the average for retinopathic arterial networks was 25.6+/−13.5 microliters per minute (p<0.001). There was no statistically significant difference between healthy venous flow and diabetic venous flow. There was a strong correlation between apparent arterial blood flow and total observable volume of arterial vessels (R=0.91) and a moderate correlation between apparent venous blood flow and total observable volume of venous vessels (R=0.57).

The frequency of lower flow rates (<$10^6$ cubic microliters/sec) was much greater in the arteries and veins of diabetic and glaucoma patients. Distributions of flow rates for all patients illustrated a left-peak-dominated bimodal shape, with the healthy patients demonstrating a much higher level of domination. The means of these peaks were also very different.

Diabetic retinopathy demonstrated significant dropout, loss of the smaller vessels for both the arterial and venous networks compared to healthy subjects. For glaucoma subjects, there was not significant dropout of vessels, but there was consistent narrowing (stenosis) of the entire arterial and venous networks. These changes for the diabetic and glaucoma subjects resulted in rather dramatic reduction in the overall blood flow conductance for the retinal vasculature.

Segment Lengths and Diameters

From the arterial segment diameter analysis, we observed a shift in the vessel population toward smaller diameters for both the diabetic and glaucoma subjects. Similar shift in diameter frequencies in the venous network was demonstrated in the diabetic and glaucoma subjects. We observed a dramatic reduction in the number of arterial vessels with lengths less than 1500 for diabetic retinopathy. This was not observed for glaucoma subjects.

Segment Generation

In arterial segment generations, we observed a significant reduction in higher generation frequency (generations above 8) in diabetic retinopathy. Particularly noticeable was the complete loss of segment generations higher than approximately 20 for diabetic retinopathy. This indicated vessel dropout was most pronounced in the smaller diameter segments. Dropout was also observed in the venous network of diabetic subjects for generations above approximately 15.

Asymmetry Indices

For arterial asymmetry indices, we observed a lower frequency of indices between 0.8 and 1 for diabetic and glaucoma patients and a higher frequency of indices between 0 and 0.3 for diabetic and glaucoma patients. For venous asymmetry indices, there were also a high frequency of indices between 0 and 0.3 for diabetic and glaucoma patients.

Bifurcation Angles

For arterial bifurcation angles, there was a higher frequency of smaller angles in diabetic and glaucoma patients. Venous bifurcation angles in healthy patients tended to have a higher frequency at the mean of the distribution as compared to diabetic and glaucoma patients.

Bifurcation Frequency in Regions of Interest

Further analysis of the diabetic retinopathy subjects in the region of interest near the fovea showed a significant decrease in the number of bifurcations between 400 and 1000 pixels. In the region near the optic disc, we saw a significant reduction in the number of bifurcations within 250 pixels of the optic disc center for glaucoma and a decrease in bifurcations between 400 and 1000 pixels for diabetic retinopathy. These new analysis tools and resultant biomarkers will have tremendous utility in many different areas of medicine including early disease detection, disease intervention strategies, outcome measures, etc. They will also be very useful for new drug/indication development for pharmaceutical and biotech companies. The reason for the amazing power of these new tools is in the amount of information that is contained in the biomarker about the health status of the entire vessel network. This is the fundamental premise of the new scientific discipline in medicine called systems medicine. The objective of this discipline is to develop mathematical constructs for entire organ systems that will capture detailed information about the health and disease states of the organ and help identify the changes in the organ and support systems which cause disease or change due to disease. Current medical science uses very large images (photographic, CT, MRI, ultrasound, PET, Xray, etc) to aid disease diagnosis and treatment. The images usually contain gigabits of data that are then condensed/compressed down into a clinical grading schema of normal, mild, moderate and severe with other descriptive annotations about the important features on the image. This dramatic data compression is too great to provide what could be called "unique solutions" for each clinical grade.

Through systems medicine frameworks one is able to condense the complex interacting processes occurring in the organ of interest (in this case the retina) into a systems of mathematical and engineering models that provide "unique solutions" aka biomarkers to each diagnostic image. Effectively, each image is compressed into biomarkers which are able to describe the salient features of the image using Kilobits or Megabits of data rather than Gigabits. This data compression makes storage, management, aggregation, interpretation of the images much easier and ultimately will make it more convenient for the doctor so he will be more likely to use the images, thus improving patient standard of care.

Manual methods include examination by an ophthalmologist or a trained retina specialist. This process is qualitative, time-consuming and labor-expensive. Proper evaluation of a fundus image may take days to weeks, as these images are often sent to off-site reading centers. By automatically identifying biomarkers in the retinal vasculature, screening will be fast, automated, and quantitative. This essentially provides a tool for doctors to look for risk factors based on a patient's vascular data, analogous to a lipid panel.

Current automatic methods focus on lesion detection in fundus images, such as cotton wool spots, drusen, or exudates, which are used almost exclusively for diabetic retinopathy. These methods do not analyze the vascular shape or structure, which can play a key role in detecting other ophthalmic diseases such as glaucoma or central retinal vein occlusion, or systemic diseases such as multiple sclerosis.

Upon diagnosis of a particular disorder in the body's vascular system, the disorder may be treated by using one of the following: prescribing a course of treatment or therapy that involves the administering of dosages of medicine, deploying stents to improve the flow of vascular fluids, performing surgery, performing surgery that includes bypass surgery, construction of models to mimic the degradation of the vascular system, construction and replacement of a part of the body with synthetic prosthetics that replicate the existing diseased part, construction and replacement of a part of the body with synthetic prosthetics that are based on the use of constructal principles (which do not necessarily replicate the diseased part), and the like.

Example 2

In this example, retinal fundus imaging is used as a modality to document the health of the retina. Retinal fundus imaging is widely used to diagnose ocular diseases such as glaucoma. Qualitative assessments of optical nerve head structures and the inherent subjectivity can lead to considerable inter- and intra-observer variability. However, quantitative parameters such as those detailed herein can help make assessments more objective, reproducible and lead to a reduction of the observer variability thus potentially improving disease detection and patient follow-up. Literature reports have indicated that retinal blood flow is often compromised in a meaningful percentage of glaucoma patients. Two suggested mechanisms for vascular dysfunction are increased resistance to flow and/or reduced perfusion pressure. A new method of automatically classifying blood flow capacity of retinal vascular networks into healthy or glaucoma categories has been developed. This telemedical based system uses a mathematical framework based on Constructal principals to automatically provide quantitative biomarkers of the retinal vasculature that are reliable for distinguishing between healthy and glaucoma subjects.

The image dataset include the following:
High-resolution color fundus images; 2336×3504 pixels
15 healthy and 15 glaucomatous patients
Source the University of Erlangen-Nuremburg (http://www5.cs.fau.de/research/data/fundus-images/).
Fovea-centered and 60 degree field of view.
Arterial/venous networks characterized using Constructal metrics, flow and rheological parameters, and morphological features.

Arteriovenous Separation

The original fundus images were segmented to isolate vessels in the vascular network. These vessels were then semi-automatically classified as arteries or veins through classification rules based on geometry, intensity and morphology. Anastomosis does not occur except on the capillary level, which results in a dichotomously branching pattern until the capillaries are reached. A wide selection of biomarkers were identified for the arterial and venous networks from each image.

Conductance Determination

Figure 5:
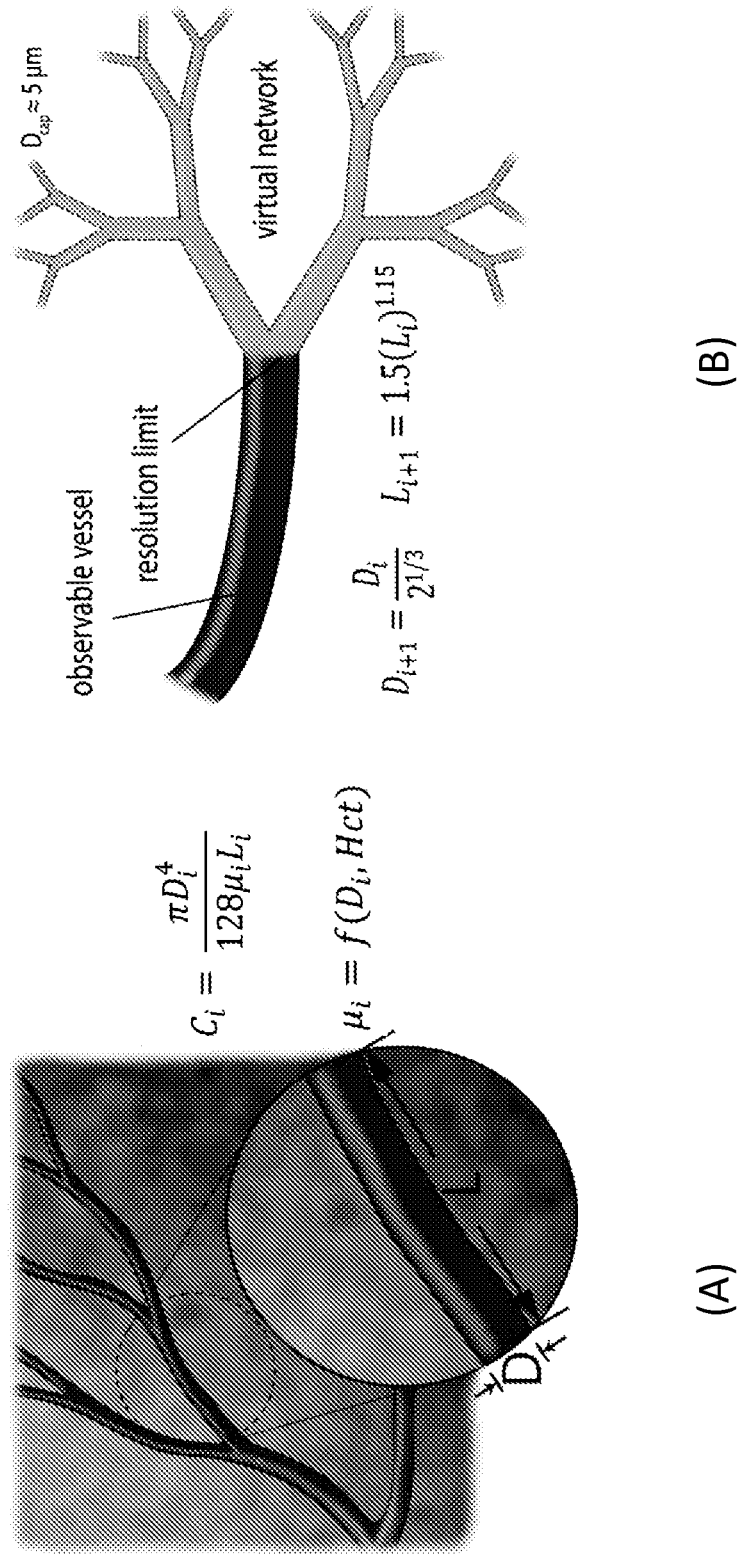
FIG. 5A shows the entire vessel and the vessel segment used for its biomarker parameters.
FIG. 5B depicts how the length and width were measured from the segmented image while the rheological properties were calculated based on the vessel diameter.

Fluid conductance was calculated for each vessel segment based on the geometry of the overall vessel networks. The length and width were measured from the segmented image while the rheological properties were calculated based on the vessel diameter. This is shown in the FIGS. 5(A) and 5(B). The method of calculating the total conductance is similar to finding an equivalent resistance in an electrical resistor network. A virtual network is appended to every endpoint in the fundus image to bridge the gap between observable blood vessels and the capillaries. Based on the observable endpoint diameter, a branching tree was created from empirical data grounded in Constructal principles.

Figure 6:
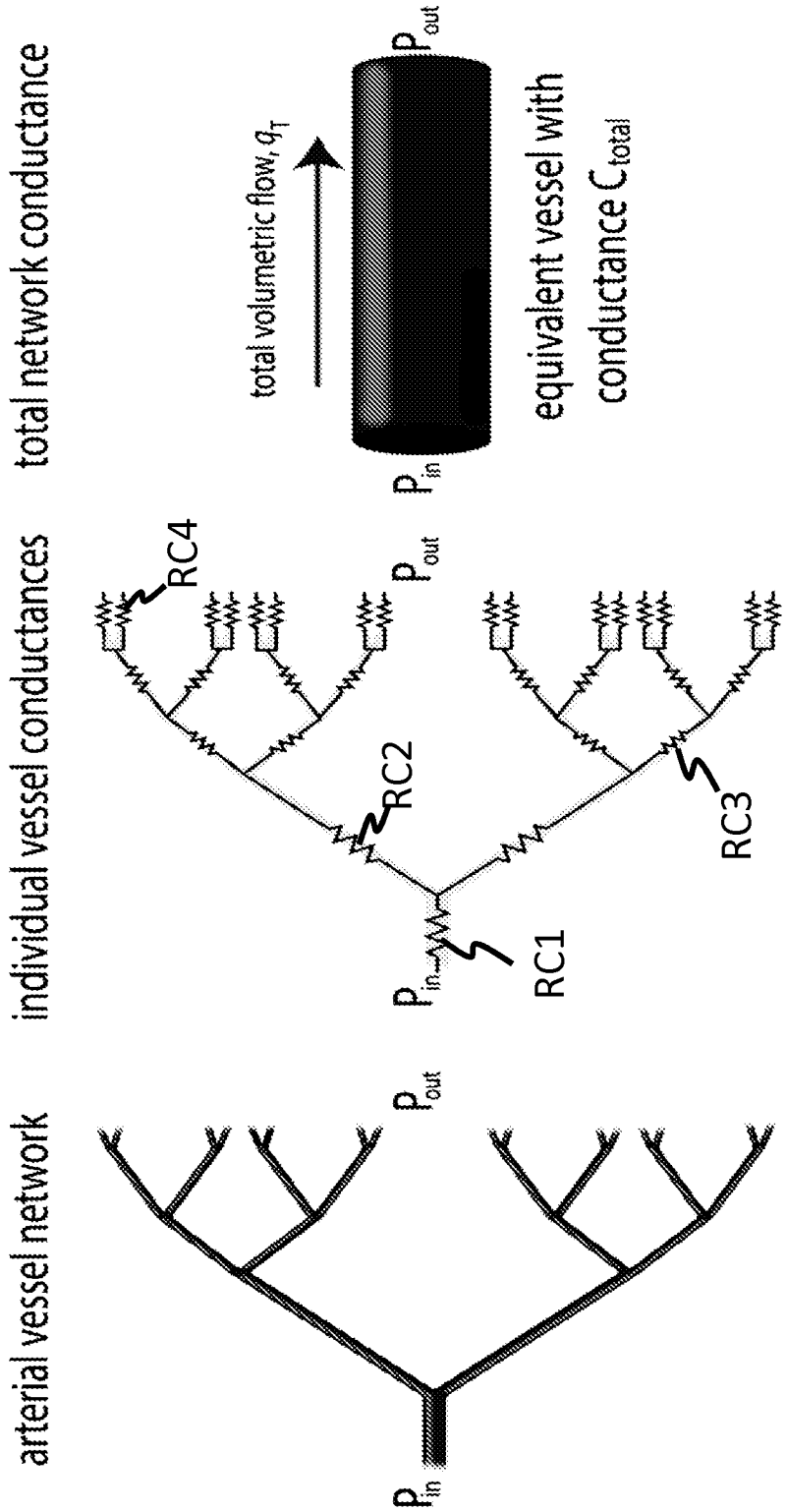
FIG. 6 shows how the connectivity of the vascular network is determined and how the cumulative effective network conductance is calculated.

The connectivity of the vascular network was determined and the cumulative effective network conductance was calculated. The method of calculating the total conductance is similar to finding an equivalent resistance in an electrical resistor network. A virtual network was appended to every endpoint in the fundus image to bridge the gap between observable blood vessels and the capillaries. This is depicted in the FIG. 6. Resistances RC1, RC2, RC3 and RC4 are shown in the FIG. 6.

Statistical Methods

Receiver Operating Characteristics (ROC) curves were prepared for each of the variables. Threshold selection was based on the Youden criteria. If more than one threshold met the criteria then the one meeting a criteria with the greatest sensitivity was chosen as threshold. Principal Components Analysis (PCA) was used to reduce the variables to a set of orthogonal components. Varimax rotation was used to achieve a simplified structure. ROC analysis was then conducted on the rotated factors.

Analysis procedures indicated a large difference often existed between healthy and glaucomatous eyes as evidenced by the overall network flow rates. The healthy arterial networks had an average flow capacity of 1.50±0.74 µL/kPa-s while the glaucomatous arterial networks had an average flow that was reduced by 70% to 0.43±0.16 µL/kPa-s. PCA identified four rotated components (shown below for arteries) with eigenvalues greater than 1.0 (Scree plot below). As demonstrated by ROC analysis, only one factor was necessary to achieve excellent precision (Sensitivity 1.00/Specificity 0.93) in detecting glaucoma patients. This factor was primarily correlated with Diameter, Larger Child Diameter, Parent Diameter, Smaller Child Diameter, Reynolds Number and Velocity. Factor structures with loadings less than 0.7 were omitted from the table below. Similar computations for the venous network identified four rotated factors with a Scree value greater than 1.0. Venous ROC analysis on RC1 yielded a Sensitivity of 0.80 and Specificity of 0.93. This is shown in the Table 1 below.

TABLE 1

|  | RC1 | RC2 | RC4 | RC3 |
|---|---|---|---|---|
| asymmetry.index.Mean |  |  |  |  |
| bifurcation.angle.Mean |  |  |  |  |
| child.area.to.parent.area.Mean |  |  | 0.90 |  |
| diameter.Mean | 0.90 |  |  |  |
| flowrate.Mean | 0.98 |  |  |  |
| junction.exponent.Mean |  |  |  | −0.81 |
| larger.child.diameter.Mean | 0.92 |  |  |  |
| larger.deviation.angle.Mean |  |  |  |  |
| length.Mean |  | −0.84 |  |  |
| parent.diameter.Mean | 0.94 |  |  |  |
| pressure.drop.Mean |  |  |  |  |
| reynolds.number.Mean | 0.98 |  |  |  |
| smaller.child.diameter.Mean | 0.82 |  |  |  |
| smaller.deviation.angle.Mean |  |  |  | 0.83 |
| tortuosity.Mean |  |  | 0.72 |  |
| velocity.Mean | 0.98 |  |  |  |
| conductance | 0.76 |  |  |  |
| n.vessel |  | 0.96 |  |  |
| n.junction |  | 0.96 |  |  |
| Eigenvalue | 7.81 | 3.31 | 3.28 | 2.28 |
| Prop.Var. | 0.41 | 0.17 | 0.17 | 0.12 |
| Cum.Prop.Var. | 0.41 | 0.58 | 0.76 | 0.88 |

Ocular blood flow deficiency associated with glaucomatous patients has been suggested in the medical literature as a cause of optic nerve damage, either directly or indirectly through raised intraocular pressure. This example provides strong biomarker signals in a broad selection of arterial and venous geometric and blood flow metrics. These features clearly highlight the diminished flow capacity of the retina vasculature in glaucomatous patients due to a global narrowing of the arterial and venous networks. Other strong biomarker signals include: artery and vein vessel diameters, artery tortuosity, artery and vein asymmetry index, artery bifurcation angle.

These biomarkers are used in conjunction with PCA to identify a set of factors providing a high sensitivity/specificity toward glaucoma patients. The Scree Plots identified 4 principal arterial components providing independent "orthogonal" information about the vessel networks. With just the first principal component, the AUC under the ROC curve was 0.973 indicating excellent accuracy is achieved for distinguishing between healthy and glaucoma patients.

It is clearly seen from the use of PCA that changes in vascular features such as blood flow, vessel diameters and lengths, tortuosity are all important metrics for distinguishing between normal and diseased patients. For the first time, Constructal analysis is able to provide a mathematical framework where the entire arterial and venous networks can be incorporated into the diagnostic decision making process.

By identifying and measuring vessels in the vascular network using automated segmentation and separation algorithms combined with the constructal framework, it is possible to calculate flow and geometric features that are reliable biomarkers to aid identification of glaucoma patients. It is believed that broad implementation of this telemedical screening tool will aid in the early identification and treatment of glaucoma patients. Extension of these biomarker concepts to other retinal vascular diseases may serve as useful tools in screening for diabetic retinopathy, hypertension, or CRVO. Because the Constructal analysis depends on precise vessel geometry and connectivity, high quality fundus images in conjunction with accurate network segmentation and separation are essential steps in achieving excellent disease identification.

In summary, this disclosure describes a method and software tool for providing visually-rich, quantitative information to interested individuals or groups, allowing for quick and effective decision-making based on the measured data. The method rapidly shows the spatial distributions of a resource or quantity spread among many sub-divided areas of a larger zone.

The uses of this disclosure are potentially as follows: Determining the amount of police officers (resource intensity) to devote to police precincts (areas of responsibility) across a metropolitan area based on historical and real-time crime data. Establishing the amount of power (resource intensity) moving through an electrical network serving locations of demand (areas of responsibility) helping to determine new powerline distribution paths. Measuring the amount of neural activity (resource intensity) inside a human brain and mapping it according to location inside the brain as a function of physical activity in order to study motor-neuron deficiency relationships. Counting the number of vehicles exiting interstate off-ramps based on exit location in order to plan next exit locations or devise new traffic-control schemes. In short, the system and method disclosed herein may be used to determine the amount of resources that need to be devoted to an area where the resources can be utilized. It can also be used to determine the time periods for which these resources are to be utilized as well as the frequency of utilization.

While this disclosure describes exemplary embodiments, it will be understood by those skilled in the art that various changes can be made and equivalents can be substituted for elements thereof without departing from the scope of the disclosed embodiments. In addition, many modifications can be made to adapt a particular situation or material to the teachings of this disclosure without departing from the essential scope thereof. Therefore, it is intended that this disclosure not be limited to the particular embodiment disclosed as the best mode contemplated for carrying out this disclosure.

What is claimed is:

1. A method comprising:
   imaging a network section through which flow occurs; where the flow is selected from a group consisting of fluid, electrons, protons, neutrons and holes; where the network section is part of a vascular network;
   partitioning the image into sub-regions based on metabolic need and function; where each region comprises one or more sources and one or more sinks; where the flow emanates from the source and exits into the sinks;
   performing a Delaunay triangulation tessellation on one or more sub-regions by connecting one or more sources and one or more sinks; where the Delaunay triangulations maximize the minimum angle of all the angles of the triangles in the triangulation;
   generating a Voronoi diagram from the Delaunay triangulation by subdividing the sub-regions into Voronoi cells, where each Voronoi cell contains exactly one sink or one source; and where the intersections of Voronoi cells are Voronoi cell vertices;
   locating a sink endpoint centroid;
   connecting a source to a nearest Voronoi cell vertex;
   connecting at least one sink to at least one of the remaining Voronoi cell vortices to complete the network; and
   performing a smoothing function on the network to form a smoothed network.

2. The method of claim 1, where the Voronoi cell vertex locations in space are points which are simultaneously equidistant from arterial sink locations.

3. The method of claim 1, further comprising comparing the smoothed network with another network.

4. The method of claim 1, further comprising comparing a parameter of the smoothed network with another network.

5. The method of claim 1, where the vascular network is a part of the brain, the heart, the lung, or the eyes of a living being.

6. The method of claim 5, where the vascular network is analyzed using biomarkers.

7. The method of claim 6, where the biomarkers pertain to an artery or to a vein; and where the biomarkers are segment diameters, segment lengths, segment generations, asymmetry index, segment flow rates, bifurcation angles, total vessel (artery or vein) volumes, junction (branching) exponents, segment tortuosities, overall network tortuosity, apparent network conductance, junction locations in relation to outer diameter/fovea, junction spatial distributions, vessel terminus locations, vessel terminus spatial distributions, vessel dropout, vessel stenosis of the artery or vein, or a combination thereof.

8. A system for performing a constructal analysis, the system comprising a processor and a memory to perform a method comprising:
   initiating capture of an image of an apparent random pathway, pattern, or network in a subject; where the apparent random pathway, pattern or network comprises a flow field; where the apparent random pathway, pattern, or network is a vascular network of blood vessels in a living being;
   partitioning the image into sub-regions based on metabolic need and function; where each region comprises one or more sources and one or more sinks; where the flow emanates from the source and exits into the sinks;
   performing a Delaunay triangulation tessellation on one or more sub-regions by connecting one or more sources and one or more sinks; where the Delaunay triangulations maximize the minimum angle of all the angles of the triangles in the triangulation;
   generating a Voronoi diagram from the Delaunay triangulation by subdividing the sub-regions into Voronoi cells, where each Voronoi cell contains exactly one sink or one source;
   and where the intersections of Voronoi cells are Voronoi cell vertices;
   locating a sink endpoint centroid;
   connecting a source to a nearest Voronoi cell vertex;
   connecting at least one sink to at least one of the remaining Voronoi cell vortices to complete the network; and
   performing a smoothing function on the network to form a smoothed network.

9. The system of claim 8, where the system is used to evaluate automated fundus photographic analysis algorithms of a computer-assisted diagnostic system for grading diabetic retinopathy, to evaluate therapeutic responses of anti-angiogenic drugs in choroidal neovascularization, to evaluate optic neuritis along with degeneration of the retinal nerve fiber layer that is highly associated with multiple sclerosis, to evaluate ocular migraines associated with systemic vascular disease and high blood pressure, to evaluate the condition of blood vessels and/or nerves when affected by hypertension, chronic kidney failure, atherosclerosis, pulmonary diseases such as emphysema, chronic bronchitis, asthma, chronic obstructive pulmonary disease, interstitial lung disease and pulmonary embolism, cardiovascular diseases, myocardial infarction, aneurysms, transient ischemic attack, brain diseases, concussions, Alzheimer's disease and/or strokes.

10. The system of claim 8, where the vascular network of blood vessels are present in a retina, a heart, a brain, breast, kidney, and/or a lung of a human being.

11. The system of claim 8, where the image is obtained using magnetic resonance imaging, computed tomography, ultrasound, ultrasound thermography, opto-acoustics, infrared imaging, positron emission tomography, or xray imaging.

12. The system of claim 8, where the image is further subjected to at least one of filtering, thresholding, digitization, and image and/or feature recognition.

13. The system of claim 8, further comprising deriving at least one quantitative measure from the smoothed network.

14. The system of claim 13, where the at least one quantitative measure is an end to end distance of the apparent random pathway, pattern, or network; an end to end distance of a portion of the apparent random pathway, pattern, or network; a radius of gyration of at least one branch or a plurality of branches of the apparent random pathway, pattern, or network; a persistence length of a branch or a plurality of branches of the apparent random pathway, pattern, or network; an average length between branches of the apparent random pathway, pattern, or network; an average branch length of the apparent random pathway, pattern, or network; an average orientation of the apparent random pathway, pattern, or network with respect to another apparent random pathway, pattern, or network; or the tortuosity of a branch or a plurality of branches of the apparent random pathway, pattern, or network.

15. The system of claim 8, where the network section is part of a vascular network.

16. The method of claim 15, where the vascular network is a part of the brain, the heart, the lung, or the eyes of a living being.

17. The method of claim 16, where the vascular network is analyzed using biomarkers.

* * * * *